(12) United States Patent
Resconi et al.

(10) Patent No.: US 6,268,518 B1
(45) Date of Patent: Jul. 31, 2001

(54) METALLOCENE COMPOUNDS AND THEIR USE IN CATALYSTS FOR THE POLYMERIZATION OF OLEFINS

(75) Inventors: Luigi Resconi; Davide Balboni, both of Ferrara (IT); Vu Anh Dang, Bear; Lin-Chen Yu, Hockessin, both of DE (US)

(73) Assignee: Montell Technology Company B.V. (NL)

( * ) Notice: Subject to any disclaimer, the term of this patent is extended or adjusted under 35 U.S.C. 154(b) by 0 days.

(21) Appl. No.: 09/050,607

(22) Filed: Mar. 30, 1998

(30) Foreign Application Priority Data

Mar. 29, 1997 (EP) .................................................. 97200933
Jun. 30, 1997 (EP) .................................................. 97201986

(51) Int. Cl.[7] .............................. C07F 17/00; C07F 7/00; C07F 4/64; B01J 31/00
(52) U.S. Cl. .................................. 556/43; 556/47; 556/53; 556/58; 526/160; 526/943; 526/351; 502/103; 502/117; 585/360; 585/361
(58) Field of Search .................................. 556/43, 47, 53, 556/58; 502/103, 117; 526/160, 35, 943; 585/360, 361

(56) References Cited

U.S. PATENT DOCUMENTS

| 5,670,681 | 9/1997 | Kuber et al. | 556/53 |
| 5,698,645 | * 12/1997 | Weller et al. | 526/160 |
| 5,786,433 | * 7/1998 | Tomotsu et al. | 526/153 |
| 5,945,553 | * 8/1999 | Kuber et al. | 556/53 |

FOREIGN PATENT DOCUMENTS

| 196 37 669 A1 | 3/1998 | (DE) . |
| 0 416 566 A2 | 3/1991 | (EP) . |
| 0 751 143 A2 | 1/1997 | (EP) . |
| WO 96/22995 | 8/1996 | (WO) . |

OTHER PUBLICATIONS

Derwent English language abstract of EP 0 416 566 A2 (1997).
Luttikhedde, et al., Synthesis and molecular structure of rac–methylenebis (4,5,6,7–tetrahydro–1–indenyl) titanium dichloride, *Journal of Organometallic Chemistry*, vol. 547, pp. 129–132 (1997).
Ewen, et al., Chemical Abstracts, vol. 116, No. 16, abstract No. 152458 (1992).

* cited by examiner

*Primary Examiner*—Porfirio Nazario-Gonzalez
(74) *Attorney, Agent, or Firm*—Bryan Cave LLP; Maurice B. Stiefel

(57) ABSTRACT

It is disclosed a new class of bridged metallocene compounds of formula (I):

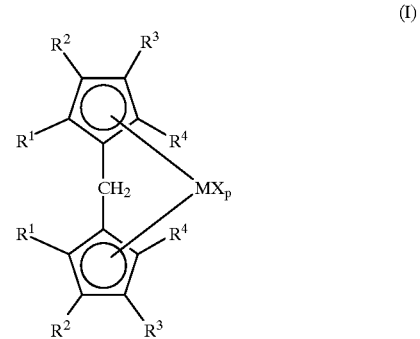

wherein $R^1$ and $R^2$ can be hydrogen, alkyl, cycloalkyl, aryl, alkylaryl or arylalkyl radicals; $R^3$ and $R^4$ form a condensed, 5- to 8-membered, aliphatic, aromatic or heterocyclic ring; M is a transition metal of groups 3, 4, 5, lanthanide or actinide; X is hydrogen, halogen, —R, —OR, —OSO$_2$CF$_3$, —OCOR, —SR, —NR$_2$ or PR$_2$, wherein R is an hydrocarbon substituent; and p is 0–3. Furthermore, a catalyst system for olefin polymerization based on the above bridged metallocene compounds and the ligands for their preparation are disclosed.

14 Claims, No Drawings

METALLOCENE COMPOUNDS AND THEIR USE IN CATALYSTS FOR THE POLYMERIZATION OF OLEFINS

FIELD OF THE INVENTION

The present invention relates to a new class of bridged metallocene compounds, to the process for their preparation and to a catalyst for the polymerization of olefins containing them. The invention also relates to a novel class of ligands useful as intermediates in the synthesis of said metallocenes.

PRIOR ART DISCLOSURE

Metallocene compounds with two bridged cyclopentadienyl groups are known as catalyst components for the polymerization of olefins.

For example, the European Patent Application EP 0 129 368 describes a catalyst system for the polymerization of olefins which comprises a bis-cyclopentadienyl coordination complex with a transition metal, wherein the two cyclopentadienyl groups can be joined by a bridging group. In this type of metallocene compounds the two cyclopentadienyl groups are generally bridged by divalent radicals having two or more carbon atoms, such as an ethylene group, or with atoms other than carbon, such as a dimethyl-silanediyl group.

Metallocene compounds having two cyclopentadienyl groups bridged by a single carbon atom are also known. In particular, metallocene compounds of this type having two different cyclopentadienyl groups are known.

For example, the European Patent Application EP 0 351 392 describes a catalyst which can be used for the preparation of syndiotactic polyolefins and contains a metallocene compound with two cyclopentadienyl groups linked by a bridge between them, in which one of the two cyclopentadienyl groups is substituted in a different manner from the other. The compound indicated as being preferred is isopropylidene(fluorenyl)(cyclopentadienyl) hafnium dichloride.

As regards metallocene compounds having two equally substituted cyclopentadienyl groups bridged by a single carbon atom, the European Patent Application EP 0 416 566 describes a process for the polymerization of α-olefins, carried out in liquid monomer, in the presence of a catalyst consisting of an alumoxane and a metallocene compound wherein the two cyclopentadienyl rings, the same or different from each other, are bridged by a —CR$_2$— divalent group, R being broadly defined, and preferably being an alkyl or an aryl group. The two compounds indicated as being preferred are Ph$_2$C-bis(indenyl)ZrCl$_2$ and (CH$_3$)$_2$C-bis(indenyl)ZrCl$_2$, the latter compound being the only metallocene actually synthesized said application and used in the polymerization of propylene, in order to produce low molecular weight polypropylene waxes.

In the International Application WO 96/22995 a class of metallocene compounds having two equally substituted cyclopentadienyl groups bridged by a —CR$_2$— divalent group is disclosed. The definitions given for the R substituents do not encompass the case in which both the R substituents are hydrogen atoms. By polymerizing propylene in the presence of a catalyst based on these metallocenes, highly isotactic polypropylenes with high molecular weights are obtained. However, the molecular weights that can be obtained at polymerization temperatures of industrial interest are still too low for many utilizations, for example for the preparation by extrusion of thick articles, such as pipes.

Therefore, it would be desirable to improve the class of one-carbon-bridged metallocenes by providing novel compounds which, when used in catalysts for the polymerization of olefins, could allow to widen the range of obtainable molecular weights.

J. A. Ewen et al. (*Macromol. Chem.; Macromol. Symp.* 48/49, 253–295, 1991) characterized a series of Group IV metallocenes possessing chiral ligand environments in order to evaluate the relationship existing between their structure and their stereospecificity, and in particular their isotacticity in propylene polymerization. Among the metallocenes used there is methylene-bis(indenyl)hafnium dichloride, which gives polypropylene with low isotacticity.

The European patent application EP 0 751 143 describes a process for the preparation of carbon-bridged bis-cyclopentadienyl compounds by reacting, in a two- or more-phases system, one or two cyclopentadienyl compounds with a carbonyl compound in the presence of a base and of a phase-transfer catalyst. Among the large number of bridged metallocenes obtainable with said process, methylene-bis(4-phenyl-1-indenyl)zirconium dichloride, methylene-bis(4-isopropyl-1-indenyl)zirconium dichloride and methylene-bis(4,5-benzo-1-indenyl)zirconium dichloride are mentioned as illustrative examples; nevertheless, neither their synthesis nor their use in olefin polymerization is reported.

SUMMARY OF THE INVENTION

The Applicant has now unexpectedly found a novel class of metallocenes having two identical cyclopentadienyl groups linked to one another by a methylene group; said metallocenes can advantageously be used as catalyst components for the polymerization of olefins.

Therefore, according to a first aspect, the present invention provides a bridged metallocene compound of formula (I):

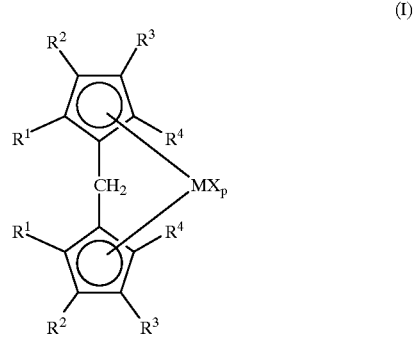

wherein:
the substituents $R^1$ and $R^2$, the same or different from each other, are selected from the group consisting of hydrogen atoms, linear or branched, saturated or unsaturated $C_1$–$C_{20}$-alkyl, $C_3$–$C_{20}$-cycloalkyl, $C_6$–$C_{20}$-aryl, $C_7$–$C_{20}$-alkylaryl and $C_7$–$C_{20}$-arylalkyl radicals, optionally containing Si or Ge atoms;
the substituents $R^3$ and $R^4$ form a condensed, 5- to 8-membered, aliphatic, aromatic or heterocyclic ring, optionally substituted, with the proviso that, when $R^1$ and $R^2$ are hydrogen atoms and said condensed ring is a benzene ring, the benzene ring is substituted in the position ortho or meta with respect to the carbon atom of the cyclopentadienyl group linked to $R^4$;

M is a transition metal belonging to groups 3, 4 or 5, or to the lanthanide or actinide groups of the Periodic Table of the Elements (new IUPAC notation);

the groups X, the same or different from each other, are monoanionic sigma ligands selected from the group consisting of hydrogen, halogen, —R, —OR, —OSO$_2$CF$_3$, —OCOR, —SR, —NR$_2$ and PR$_2$ groups, wherein the R substituents are $C_1$–$C_{20}$-alkyl, $C_3$–$C_{20}$-cycloalkyl, $C_2$–$C_{20}$-alkenyl, $C_6$–$C_{20}$-aryl, $C_7$–$C_{20}$-alkylaryl or $C_7$–$C_{20}$-arylalkyl radicals, optionally containing Si or Ge atoms; and p is an integer ranging from 0 to 3, being equal to the oxidation state of the metal M minus two.

It is another object according to the present invention a ligand of formula (II):

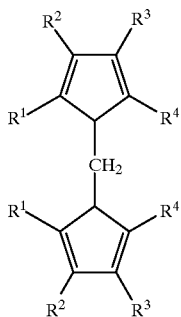

(II)

and its double bond isomers, wherein $R^1$, $R^2$, $R^3$ and $R^4$ have the meaning reported above, with the exclusion of bis(3-t-butyl-indenyl)methane, said ligand being useful in the preparation of said bridged metallocene compounds of formula (I).

Furthermore, the present invention concerns a process for the preparation of the metallocene compounds of formula (I), as well as a catalyst system for the polymerization of olefins comprising the product obtainable by contacting:

(A) one or more bridged metallocene compounds of formula (d), as described above, and (B) a suitable activating cocatalyst.

Finally, the present invention provides a process for the polymerization of olefins comprising the polymerization reaction of one or more olefinic monomers in the presence of a catalyst system as described above.

DETAILED DESCRIPTION OF THE INVENTION

The characteristics and advantages of the bridged metallocene compounds of formula (I), the process for their preparation, the catalyst system containing them, their use in the polymerization of olefins and the ligands of formula (II), according to the present invention, will be better described in the following detailed description.

In the bridged metallocene compound of formula (I), according to the present invention, the substituents $R^3$ and $R^4$ preferably form a condensed benzene ring, optionally substituted; the transition metal M is preferably Ti, Zr or Hf; the X substituents are preferably chlorine or methyl; p is preferably 2.

A particularly interesting subclass (subclass (a)) of bridged metallocene compounds, according to the present invention, is represented by the compound of formula (I) wherein the substituents $R^3$ and $R^4$ form a condensed benzene ring substituted in 3 position; more specifically, said compounds are bridged bis-indenyl compounds of formula (III):

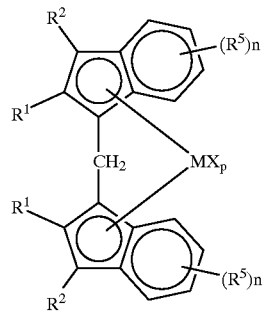

(III)

wherein:

$R^1$, $R^2$, M, X and p have the meaning reported above, with the proviso that $R^2$ is different from hydrogen;

the $R^5$ substituents, the same or different from each other, are selected from the group consisting of linear or branched, saturated or unsaturated, $C_1$–$C_{20}$-alkyl, $C_1$–$C_{20}$-cycloalkyl, $C_6$–$C_{20}$-aryl, $C_7$–$C_{20}$-alkylaryl and $C_7$–$C_{20}$-arylalkyl radicals, optionally containing Si or Ge atoms, or two vicinal $R^5$ substituents form a ring having from 5 to 8, preferably 6, members;

and n is an integer ranging from 0 to 4. Examples of suitable compounds of formula (III) belonging to subclass (a) are:

methylene-bis(3-methyl-1-indenyl)zirconium dichloride or dimethyl, methylene-bis(3-ethyl-1-indenyl)zirconium dichloride or dimethyl, methylene-bis(3-isopropyl-1-indenyl)zirconium dichloride or dimethyl, methylene-bis(3-dimethylsilil-1-indenyl)zirconium dichloride or dimethyl, methylene-bis(3-diethylsilil-1-indenyl)zirconium dichloride or dimethyl, methylene-bis(3-phenyl-1-indenyl)zirconium dichloride or dimethyl, and methylene-bis(3-phenyl-4,6-dimethyl-1-indenyl) zirconium dichloride or dimethyl.

Particularly interesting metallocene compounds of formula (III) are those compounds wherein $R^2$ is a C, Si or Ge atom, substituted with three linear or branched, saturated or unsaturated, $C_1$–$C_{10}$ alkyl, $C_1$–$C_{12}$ cycloalkyl, $C_6$–$C_{12}$ aryl, $C_7$–$C_{12}$ alkylaryl or $C_7$–$C_{12}$ arylalkyl groups, and $R^1$, $R^5$, M, X, n, and p have the meaning reported above. Suitable $R^2$ substituents of this kind are tert-butyl, trimethylsilyl, trimethylgermyl, 2,2-dimethyl-propyl and 2-methyl-2-phenyl-ethyl groups, the tert-butyl group being particularly preferred. Examples of particularly preferred bridged metallocene compounds belonging to subclass (a) are:

methylene-bis(3-t-butyl-1-indenyl)zirconium dichloride or dimethyl, methylene-bis(3-trimethylsilyl-1-indenyl)zirconium dichloride or dimethyl, methylene-bis(3-trimethylgermyl-1-indenyl)zirconium dichloride or dimethyl, methylene-bis(2-methyl-3-t-butyl-1-indenyl)zirconium dichioride or dimethyl, methylene-bis(2-methyl-3-trimethylsilyl-1-indenyl) zirconium dichloride or dimethyl, methylene-bis(2-methyl-3-trimethylgermyl-1-indenyl) zirconium dichloride or dimethyl, methylene-bis(3-t-butyl-5,6-dimethyl-1-indenyl) zirconium dichloride or dimethyl, methylene-bis(3,5-di-t-butyl-1-indenyl)zirconium dichioride or dimethyl, methylene-bis(3,6-di-t-butyl-1-indenyl)zirconium dichloride or dimethyl, methylene-bis[3-(2,2-dimethyl-propyl)-1-indenyl] zirconium dichloride or dimethyl, and methylene-bis[3-(2-methyl-2-phenyl-ethyl)-1-indenyl] zirconium dichloride or dimethyl.

A particularly preferred metallocene is rac-methylene-bis (3-t-butyl-indenyl)zirconium dichloride.

An advantageous property of this particular class of metallocenes of formula (III) having bulky $R^2$ substituents is that the meso isomeric form, when present, is generally not active in the polymerization of olefins and thus need not to be separated from the racemic form. Furthermore, these metallocenes give unexpectedly advantageous results in propylene polymerisation, as will be better explained hereinafter.

Another advantageous subclass (subclass (b)) of bridged metallocene compounds, according to the present invention, is represented by the bis-indenyl metallocene compounds of formula (III), as reported above, wherein $R^2$ is hydrogen and $R^1$, $R^5$, M, X, p and n have the meaning reported above. Suitable examples of metallocene compounds belonging to subclass (b) are the following:

methylene-bis(2-methyl-1-indenyl)zirconium dichloride or dimethyl, methylene-bis(2-ethyl-1-indenyl)zirconium dichloride or dimethyl, methylene-bis(2-methyl-4-phenyl-1-indenyl)zirconium dichloride or dimethyl, methylene-bis(2-ethyl-4-phenyl-1-indenyl)zirconium dichloride or dimethyl, methylene-bis[2-ethyl-4-(1-naphtyl)-1-indenyl] zirconium dichloride or dimethyl, methylene-bis(2,5,6-trimethyl-1-indenyl)zirconium dichloride or dimethyl, methylene-bis(6-t-butyl-1-indenyl)zirconium dichloride or dimethyl, methylene-bis[2-methyl-4-(1-naphtyl)-1-indenyl] zirconium dichloride or dimethyl, methylene-bis(2-methyl-acenaphtyl-1-indenyl)zirconium dichloride or dimethyl, methylene-bis(2-ethyl-acenaphtyl-1-indenyl)zirconium dichloride or dimethyl, methylene-bis(2-methyl-4,5-benzo-1-indenyl)zirconium dichloride or dimethyl, methylene-bis(2-ethyl-4,5-benzo-1-indenyl)zirconium dichloride or dimethyl.

Particularly preferred compounds of subclass (b) are characterized by the fact that $R^2$ is hydrogen and the $R^5$ groups in the positions 4 and 7 of the indenyl residues are different from hydrogen. Examples of the $R^5$ groups in the positions 4 and 7 of the indenyl are methyl, ethyl or phenyl groups. Suitable examples of these metallocene compounds are:

methylene-bis(2,4,7-trimethyl-1-indenyl)zirconium dichloride or dimethyl, methylene-bis(4,7-dimethyl-1-indenyl)zirconium dichloride or dimethyl.

It is another object of the present invention a process for the preparation of the bridged metallocene compounds of the formula (I) comprising reacting a bis-cyclopentadienyl ligand of the formula (IV):

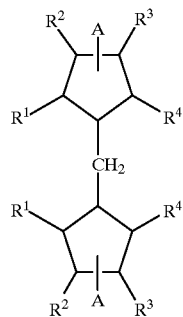

(IV)

wherein $R^1$, $R^2$, $R^3$ and $R^4$ have the meaning reported above and A is a suitable leaving group, with a compound of formula $MX_{p+2}$, wherein M, X and p are defined as above. The two double bonds in each of the cyclopentadienyl rings of the ligands of formula (IV) can be in any of the allowed positions. The leaving group A is preferably a cation of an alkaline or earth-alkaline metal, or a group —$SiR_3$ or —$SnR_3$, wherein the substituents R are $C_1$–$C_{20}$-alkyl, $C_3$–$C_{20}$-cycloalkyl, $C_2$–$C_{20}$-alkenyl, $C_6$–$C_{20}$-aryl, $C_7$–$C_{20}$-alkylaryl or $C_7$–$C_{20}$-arylalkyl radicals.

When one or more X groups of the bridged metallocene compound (I) are other than halogen, it is necessary to substitute one or more halogens of the metallocene dihalide, obtained as reported above, with one or more substituent X other than halogen. The substitution reaction can be carried out by standard procedures, for example, when X are alkyl groups, by reacting the metallocene dihalide with alkylmagnesium halides (Grignard reagents) or with alkyllithium compounds.

The spatial configuration, due to the particular bridging group of the metallocenes of the invention, does not allow the formation of the meso isomer in those metallocene compounds of formula (I) in which a α-substituent, i.e. $R^1$ and/or $R^4$, is a bulky group such as a C, Si or Ge atom, substituted with two or three linear or branched, saturated or unsaturated, $C_1$–$C_{10}$ alkyl, $C_5$–$C_{12}$ cycloalkyl, $C_6$–$C_{12}$ aryl, $C_7$–$C_{12}$ alkylaryl or $C_7$–$C_{12}$ arylalkyl groups, such as for instance a trimethyl-silyl group. This is a big advantage of some of the bridged metallocene compounds of the invention, which are directly obtainable in pure racemic form, without the need of difficult and onerous purification procedures in order to eliminate the meso isomeric form.

It is another object of the present invention a ligand corresponding to formula (II):

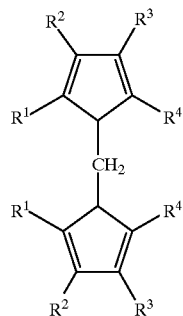

(II)

and its double bond isomers, wherein $R^1$, $R^2$, $R^3$ and $R^4$ have the meaning reported above, with the exclusion of bis(3-t-butyl-indenyl)methane.

In fact, bis(3-t-butyl-indenyl)methane is mentioned among a plethora of metallocene ligands in U.S. Pat. No. 5,459,117. This patent describes a broad class of metallocene compounds containing variously substituted cyclopentadienyl rings, where the substituents impart either $C_s$, $C_2$, pseudo-$C_s$ or pseudo-$C_2$ symmetry to the ligand.

The ligands of formula (II) can be prepared by different methods. A particularly suitable method is the one described in the European Patent Application No. 97200933.6, in the name of the same Applicant. This process allows the preparation of compounds hardly obtainable by the known methods in the state of the art, such as the compounds of formula (I) having bulky $R^1$ substituents.

The metallocene compounds of the present invention can conveniently be used as catalyst components for the polymerization of olefins. Thus, according to a further aspect, the present invention provides a catalyst system for the polymerization of olefins comprising the product obtainable by contacting:

(A) one or more bridged metallocene compounds of formula (I) or (III) as described above, and
(B) a suitable activating cocatalyst.

Said activating cocatalyst is preferably an alumoxane and/or a compound able to form an alkylmetallocene cation.

In the catalyst system according to the present invention, both said bridged metallocene compound and said alumoxane can be pre-reacted with an organometallic aluminum compound of formula $AlR^6_3$ or $Al_2R^6_6$, wherein the $R^6$ substituents, the same or different from each other, are selected from the group consisting of hydrogen, halogen, linear or branched, saturated or unsaturated $C_1$–$C_{20}$-alkyl, $C_3$–$C_{20}$-cycloalkyl, $C_6$–$C_{20}$-aryl, $C_7$–$C_{20}$-alkylaryl and $C_7$–$C_{20}$-arylalkyl radicals, optionally containing Si or Ge atoms.

Non-limiting examples of said organometallic aluminum compounds of formula $AlR^6_3$ or $Al_2R^6_6$ are:

Al(Me)$_3$, Al(Et)$_3$, AlH(Et)$_2$, Al(iBu)$_3$, AlH(iBu)$_2$, Al(iHex)$_3$, Al(iOct)$_3$, Al(C$_6$H$_5$)$_3$, Al(CH$_2$C$_6$H$_5$)$_3$, Al(CH$_2$CMe$_3$)$_3$, Al(CH$_2$SiMe$_3$)$_3$, Al(Me)$_2$iBu, Al(Me)$_2$Et, AlMe(Et)$_2$, AlMe(iBu)$_2$, Al(Me)$_2$iBu, Al(Me)$_2$Cl, Al(Et)$_2$Cl, AlEtCl$_2$ and Al$_2$(Et)$_3$Cl$_3$, wherein Me=methyl, Et=ethyl, iBu=isobutyl, iHex=isohexyl, iOct=2,4,4-trimethyl-pentyl.

Amongst the above organometallic aluminum compounds, trimethylaluminum (TMA), triisobutylaluminum (TIBAL) and tris(2,4,4-trimethyl-pentyl)aluminum (TIOA) are preferred.

When the activating cocatalyst (B) of the catalyst system of the invention is an alumoxane, it is a linear, branched or cyclic compound containing at least one group of the type:

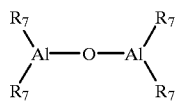

wherein the $R^7$ substituents, the same or different from each other, are selected from the group consisting of hydrogen, linear or branched, saturated or unsaturated $C_1$–$C_{20}$-alkyl, $C_3$–$C_{20}$-cycloalkyl, $C_6$–$C_{20}$-aryl, $C_7$–$C_{20}$-alkylaryl and $C_7$–$C_{20}$-arylalkyl radicals, optionally containing Si or Ge atoms, or $R^7$ is a group —O—Al($R^7$)$_2$.

In particular, linear alumoxanes have formula:

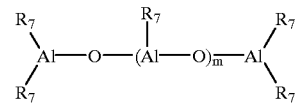

wherein m is an integer ranging from 0 to 40 and $R^7$ has the meaning reported above; and cyclic alumoxanes have formula:

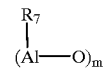

wherein m is an integer ranging from 2 to 40 and $R^7$ has the meaning reported above.

In the above-mentioned linear and cyclic alumoxanes, $R^7$ is preferably methyl, ethyl, isobutyl or 2,4,4-trimethyl-pentyl.

Examples of alumoxanes suitable as activating cocatalysts in the catalysts system according to the present invention are methylalumoxane (MAO), isobutylalumoxane (TIBAO) and 2,4,4-trimethyl-pentylalumoxane (TIOAO) and 2-methyl-pentylalumoxane. Mixtures of different alumoxanes can also be used.

Activating cocatalysts suitable as component (B) in the catalysts of the invention are also the product of the reaction between water and an organometallic aluminum compound, preferably of formula $AlR^6_3$ or $Al_2R^6_6$, wherein $R^6$ has the meaning reported above. Particularly suitable are the organometallic aluminum compounds described in EP 0 575 875 (formula (II)) and those described in WO 96/02580 (formula (II)). Non-limiting examples of organometallic aluminum compounds of formula $AlR^6_3$ or $Al_2R^6_6$ are:

| | |
|---|---|
| tris(methyl)aluminum, | tris(isobutyl)aluminum, |
| tris(isooctyl)aluminum | bis(isobutyl)aluminum hydride, |
| methyl-bis(isobutyl)aluminum, | dimethyl(isobutyl)aluminum, |
| tris(isohexyl)aluminum, | tris(benzyl)aluminum, |
| tris(tolyl)aluminum; | tris(2,4,4-trimethylpentyl) aluminum, |
| bis(2,4,4-trimethylpentyl)aluminum hydride, | isobutyl-bis(2-phenyl-propyl) aluminum, |
| diisobutyl-(2-phenyl-propyl) aluminum, and diisobutyl-(2,4,4-trimethyl-pentyl) aluminum. | isobutyl-bis(2,4,4-trimethyl-pentyl)aluminum |

Particularly preferred aluminum compounds are tris(2,4,4-trimethylpentyl)aluminum (TIOA), and triisobutylaluminum (TIBA).

Mixtures of different organometallic aluminum compounds and/or alumoxanes can also be used.

The molar ratio between aluminum and the metal M of the bridged metallocene compound is preferably comprised between 10:1 and 50,000:1, and more preferably between 100:1 and 4,000:1.

The activating cocatalyst (B) of the catalyst system of the invention, can be a compound able to form an alkylmetallocene cation; preferably said compounds have formula $Y^+Z^-$, wherein $Y^+$ is a Broensted acid, able to donate a proton and to react irreversibly with a substituent X of the metallocene compound of formula (I), and $Z^-$ is a compatible non-coordinating anion, able to stabilize the active catalytic species which results from the reaction of the two compounds and which is sufficiently labile to be displaceable by an olefin substrate. Preferably, the anion $Z^-$ consists of one or more boron atoms. More preferably, the anion $Z^-$ is an anion of the formula $BAr_4^{(-)}$, wherein the substituents Ar, the same or different from each other, are aryl radicals such as phenyl, pentafluorophenyl or bis(trifluoromethyl) phenyl. Tetrakis-pentafluorophenyl borate is particularly preferred. Moreover, compounds of the formula $BAr_3$ can conveniently be used.

The catalysts of the present invention can also be used on inert supports. This is achieved by depositing a bridged metallocene compound (A), or the product of the reaction of the compound (A) with a component (B), or the component (B) and then the metallocene compound (A), on a suitable inert support, such as silica, alumina, magnesium halides, styrene/divinylbenzene copolymers, polyethylene or polypropylene.

A suitable class of inert supports comprises porous organic supports functionalized with groups having active hydrogen atoms; particularly preferred organic supports are partially crosslinked styrene polymers, as described in the European patent application EP 0 633 272.

Another class of inert supports particularly suitable for the catalyst system according to the present invention comprises olefinic porous prepolymers, in particular propylene porous prepolymers, as described in the International patent application WO 95/26369.

A further suitable class of inert supports for use according to the invention comprises porous magnesium halides supports, as described in the International patent application WO 95/32995.

The supported catalyst system, optionally in the presence of alkylaluminum compounds, can be usefully employed in gas-phase polymerization processes.

Another advantage of the bridged metallocene compounds according to the present invention, and particularly of those having bulky substituents such as tert-butyl groups, is that they are soluble in aliphatic hydrocarbons such as pentane, isobutane, butane and propane. This property makes it easier to bring the metallocene into intimate contact with the support, particularly when this is a porous material, thus achieving a more uniform and stable fixation of the metallocene onto the support.

It is a further object of the present invention a process for the polymerization of olefins, comprising the polymerization reaction of one or more olefinic monomers in the presence of a catalyst system as described above. The catalysts according to the invention can conveniently be used, for example, in the homopolymerization of ethylene or α-olefins, such as propylene and 1-butene; in the copolymerization of ethylene with α-olefins, such as propylene, 1-butene and 1-hexene; in the copolymerization of propylene with ethylene or with $C_4$–$C_{10}$ α-olefins, such as 1-butene; in the homopolymerization of cycloolefins or in the copolymerization thereof with ethylene.

Particularly interesting results are achieved when the catalysts of the invention are used in propylene polymerization. According to a particular embodiment of the process for olefin polymerization of the invention, propylene is polymerized in the presence of the racemic isomer of a bridged metallocene compound of formula (III), subclass (a), as reported above. In fact, by polymerizing propylene in the presence of these metallocenes, it is possible to obtain in high yields, at temperatures of industrial interest (i.e. higher than 50° C.), polypropylenes having high molecular weights, narrow molecular weight distributions, high isotacticities (mmmm pentad content generally higher than 90%) and a very high levels of regioregularity. The $^{13}C$-NMR analysis carried out on propylene polymers obtained with the bridged metallocene compounds belonging to subclass (a) do not show structural units due to regioirregular insertions (R.I.). As regards the analytical methodology used, reference is made to "Macromolecules, 1995, vol. 28, page. 6667–6676".

The obtained propylene polymers have low xylene-soluble fractions, generally lower than 5% by weight, preferably lower than 3% by weight, more preferably lower than 1% by weight. In addition, these polymers are generally free from acetone-soluble fractions (atactic propylene oligomers).

According to another particular embodiment of the process according to the present invention, one or more olefins are oligomerized in the presence of the racemic isomer of a bridged metallocene compound of formula (III), subclass (b), as reported above. In fact, by polymerizing one or more olefins, and in particular propylene, in the presence of the above particular metallocenes, very low molecular weight polypropylene waxes are obtained, having fairly high isotacticities.

Particularly advantageous are the bridged metallocene compounds (III) belonging to subclass (b) wherein $R^2$ is an hydrogen atom and the $R^5$ substituents in the positions 4 and 7 of the indenyl groups are other than hydrogen atoms. Preferably, $R^1$ is an hydrogen atom. A particularly preferred metallocene compound is rac-methylene-bis(4,7-dimethyl-1-indenyl)zirconium dichloride, very advantageous in propylene oligomerization.

When the polymerization of propylene is carried out in the presence of rac-methylene-bis(4,7-dimehtyl-1-indenyl) zirconium dichloride, the molecular weight of the obtained propylene waxes is unexpectedly much lower than the molecular weight of the waxes obtained, under the same conditions, with rac-methylene-bis(1-indenyl)zirconium dichloride or with the corresponding ethylene-bridged homologue (i.e. the rac-ethylene-bis(4,7-dimethyl-indenyl) zirconium dichloride), both known in the state of the art.

Another group of advantageous bridged metallocene compounds (III), are compounds belonging to subclass (b) wherein $R^1$ is other than hydrogen, $R^2$ is hydrogen and n is 0. Even this substitution pattern gives propylene waxes having very low molecular weights.

It results thus evident that a further advantage of the bridged metallocene compounds according to the present invention is that they allow to obtain polymers having a very wide range of molecular weights. In particular, they make it possible to further increase the molecular weight when a high molecular weight polymer is desired (by using the bridged metallocene compounds belonging to subclass (a)) and to further decrease the molecular weight when the target is a low molecular weight polyolefin wax (by using bridged metallocene compounds belonging to subclass (b)).

A further advantageous characteristic of the metallocenes of the invention is that the use of a small amount of hydrogen brings about a considerable increase of the polymerization activities while not substantially affecting the molecular weights of the obtained polymers.

The process for the polymerization of olefins according to the present invention can be carried out in the liquid phase, optionally in the presence of inert hydrocarbon solvents, or in the gas phase. The hydrocarbon solvent can either be aromatic, such as toluene, or aliphatic, such as propane, hexane, heptane, isobutane or cyclohexane.

The polymerization temperature is generally comprised between −100° C. and +100° C., and preferably between 0°

C. and +80° C. The lower the polymerization temperature, the higher are the resulting molecular weights of the polymers obtained.

The molecular weight of the polymers can be varied by varying the type or the concentration of the catalyst components or using molecular weight regulators, such as hydrogen.

The molecular weight distribution can be varied by using mixtures of different metallocene compounds or by carrying out the polymerization in several stages, at different polymerization temperatures and/or different concentrations of molecular weight regulators.

The polymerization yield depends on the purity of the metallocene compound of the catalyst. The metallocene compounds obtained by the process of the invention can be used as such or can be subjected to purification treatments.

The components of the catalyst can be contacted before the polymerization step. The pre-contact concentrations are generally between 1 and $10^{-8}$ mol/l for the metallocene component (A), while they are generally between 10 and $10^{-8}$ mol/l for the component (B). The pre-contact is generally effected in the presence of a hydrocarbon solvent and, if suitable, in the presence of small quantities of monomer. In the pre-contact it is also possible to use a non-polymerizable olefin, such as isobutene, 2-butene, neohexene and the like.

The following examples are given for illustrative and not limitative purposes.

GENERAL PROCEDURES AND CHARACTERIZATIONS

The following abbreviations are used:

| | | |
|---|---|---|
| THF = tetrahydrofuran | Et$_2$O = diethyl ether | NaOEt = sodium ethoxide |
| $^t$BuOK = potassium tert-butoxide | DMSO = dimethyl sulfoxide | BuLi = butyllithium |
| DMF = N,N-dimethylformamide. | | |

All operations were performed under nitrogen by using conventional Schlenk-line techniques. Solvents were purified by degassing with N$_2$ and passing over activated (8 hours, N$_2$ purge, 300° C.) Al$_2$O$_3$, and stored under nitrogen. MeLi and BuLi (Aldrich) were used as received.

All compounds were analysed on an AC 200 Bruker spectrometer operating at 200.13 MHz for $^1$H and 50.323 MHz for $^{13}$C, by $^1$H NMR (CDCl$_3$, referenced against the peak of residual CHCl$_3$ at 7.25 ppm, or CD$_2$Cl$_2$, referenced against the peak of residual CHDCl$_2$ at 5.35 ppm,) or $^{13}$C NMR (Broad Band decoupling mode) (CDCl$_3$, referenced against the central line of CDCl$_3$ at 77.00 ppm). All NMR solvents were dried over LiAlH$_4$ or CaH$_2$ and distilled before use. Preparation of the samples was carried out under nitrogen using standard inert atmosphere techniques. Due to the low solubility of some zirconocenes, these samples were prepared as saturated solutions in 0.5 mL of solvent in a 5-mm NMR tube.

GC-MS analysis were performed on a HP MS Engine 5989B instrument.

The polymers were characterized as follows.

The $^1$H-NMR and $^{13}$C-NMR analyses were carried out on a Bruker 400 MHz instrument. The samples were analyzed as solutions in tetrachlorodideuteroethane at 130° C. The Mn values were obtained from the $^1$H-NMR by measuring the ratio between the total signal and the olefin end group signal, assuming one double bond per chain.

The intrinsic viscosity (I.V.) was measured in THN (for polyethylene) or in tetralin (for polypropylene) at 135° C.

The melting points (Tm) were measured by Differential Scanning Calorimetry (D.S.C.) on an instrument DSC-7 of Perkin Elner Co. Ltd., according to the following method:

about 10 mg of sample obtained from the polymerization were cooled to −25° C. and thereafter heated at 200° C. with a scanning speed corresponding to 10° C. minute. The sample was kept at 200° C. for 5 minutes and thereafter cooled with a scanning speed corresponding to 10° C./minute. Then, a second scanning was carried out according to the same modalities of the first one. The values reported are those obtained in the first scanning.

The molecular weight distribution was determined by GPC carried out on an instrument WATERS 150 in orthodichlorobenzene at 135° C.

METALLOCENES SYNTHESIS

Synthesis 1 rac-Methylene-bis(3-t-butyl-1-indenyl)zirconium dichloride

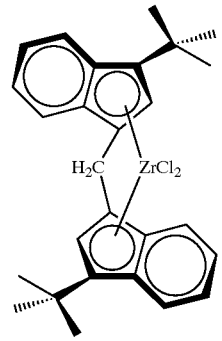

(a) Synthesis of 3-t-butyl-1-indene 42.0 g of indene (technical grade, 94% by GC, 39.5 g, 340 mmol), 50%wt. aqueous KOH (308 g in 308 mL) and 15.8 g of Adogen (Aldrich, 34 mmol), dissolved in 139.7 g of tert-butyibromide (1019.6 mmol), were introduced in this order, at room temperature, in a 1 L jacketed glass reactor with mechanical stirrer (Büichi). The organic phase turned green. The mixture was heated to 60° C., maintained under vigorous stirring for two hours (a pressure build-up to 2.5 bar-g was observed) and then cooled to room temperature. The total reaction time was 3 hours. The organic phase was extracted with technical hexane (3×200 mL) and analyzed by GC, demonstrating a conversion of 74.5%wt. of 3-tert-butyl-indene and of 1.8%wt. of 1-tert-butyl-indene, the unreacted indene being equal to 13.7%wt. The solution was evaporated under reduced pressure (rotovac) and the resulting dark brown viscous liquid was distilled at 1 mmHg, collecting the fraction boiling between 70 and 80° C. (40 g, 76.8% of 3-tert-butyl-indene and 19.5% of 1-tert-butyl-indene, no indene).

(b) Synthesis of bis(1-t-butyl-3-indenyl)methane

In a three neck, 1 L flask with stirring bar were introduced in this order: 10.32 g of $^t$BuOK (92 mmol), 400 mL of DMF, 80.6 g of tert-butyl-indene (98.2% by GC, 460 mmol), obtained as described above, and 18.6 mL of aqueous formalin (37%, 6.9 g, 230 mmol); said reactants were added dropwise over 15 minutes. A mildly exothermic reaction was observed and the solution turned red. The mixture was stirred at room temperature for 2 hours; then the reaction was quenched by pouring the mixture on ice and NH$_4$Cl, extracted with Et$_2$O (2×250 mL) and concentrated under reduced pressure, thus yielding an orange oily product having the following G.C. composition: 1-$^t$BuInd, 0.3%; 3-$^t$BuInd, 2.8%; bis(1-t-butyl-3-indenyl)methane, 78.3%; the rest being byproducts.

The yield of the raw product was 83.6 g, corresponding to a yield of 79.9%. The orange oily product crystallized upon standing (about 1 hour). The obtained product was further purified by washing with pentane, thus isolating bis(3-tert-butyl-1-indenyl)methane as a light yellow powder, 99.8% pure by G.C.

(c)(1) Synthesis of methylene-bis(3-t-butyl-1-indenyl) zirconium dichloride (in Et$_2$O/pentane)

11.0 g of pure bis(1-tert-butyl-3-indenyl)methane (30.9 mmol), obtained as described above, were dissolved in 200 mL Et$_2$O, in a 250 mL Schlenk tube, and the solution was cooled to −15° C. 40 mL of 1.6 M BuLi in hexane (63.3 mmol) were added dropwise, over 15 minutes, under stirring. The solution was allowed to warm to room temperature and stirred for 4.5 hours. An increasing turbidity developed with final formation of a yellow suspension. 7.2 g of ZrCl$_4$ (30.9 mmol) were slurried in 200 mL pentane. The two mixtures were both cooled to −80° C. and the Li salt solution in Et$_2$O was quickly added to the ZrCl$_4$ slurry in pentane. The cooling bath was removed and after 20 minutes the color of the slurry changed from yellow to red. The reaction mixture was stirred overnight at room temperature and then was brought to dryness under reduced pressure. The red powder was slurried in 200 mL of pentane and transferred into a filtration apparatus equipped with side arm (to allow solvent refluxing) connecting the system above and below the frit, a receiving flask on the bottom and bubble condenser on the top. The red solid was extracted with refluxing pentane for about 3.5 hours. The filtrate was evaporated to dryness under reduced pressure to give a red paste which contained rac-CH$_2$(3-$^t$Bu-1-Ind)$_2$ZrCl$_2$ free from its meso isomer, but containing polymeric byproducts. The paste was washed twice with Et$_2$O (20+10 mL) to give 1 g of pure product. The red solid on the frit was fuirther extracted with CH$_2$Cl$_2$ until the filtrate was light orange (6 hours) and dried. $^1$H1-NMR analysis showed the presence of pure rac-CH$_2$(3-$^t$Bu-Ind)$_2$ZrCl$_2$ (7.25 g).

The total yield (8.25 g of red powder) of rac-CH$_2$(3-$^t$Bu-Ind)$_2$ZrCl$_2$ was 52%. $^1$H NMR (CDCl$_3$, δ, ppm): s, 1.41, $^t$Bu, 18H; s, 4.78, CH$_2$, 2H; s, 5.79, 2H, Cp-H; m, 7.15, 2H, m, 7.36, 2H; m, 7.47, 2H; m, 7.78, 2H.

(c)(2) Synthesis of methylene-bis(3-t-butyl-1indenyl) zirconium dichloride (in Et$_2$O/toluene)

All operations were performed in the dark, by covering the glassware with aluminum foil.

3.46 g of bis(1-tert-butyl-3-indenyl)methane (9,6 mmol), obtained as described above, were dissolved in 60 mL Et$_2$O in a 250 mL Schlenk tube, and the solution was cooled to 0° C. 8.8 mL of 2.5 M BuLi in hexane (22.0 mmol) were added dropwise, over 6 minutes under stirring. The obtained solution was allowed to warm to room temperature and stirred for 24 hours. An increasing turbidity developed with final formation of an orange precipitate. 2.46 g of ZrCl$_4$ (10.6 mmol) were slurried in 60 mL toluene. The two mixtures were both cooled to −20° C. and the ZrCl$_4$ slurry in toluene were quickly added to the Li salt solution in Et$_2$O; instantly, the slurry turned from orange to red. The cooling bath was kept at −20° C. for 25 minutes and then at −17° C. for 20 minutes. The thus obtained solution was allowed to warm to 0° C. and, after 20 minutes, the cooling bath was removed. The reaction mixture was maintained under stirring overnight at room temperature; Et$_2$O was removed under reduced pressure and the obtained toluene suspension was filtered. The filtrate was evaporated to dryness under reduced pressure to give 3.26 g of a red powder.

$^1$H-NMR analysis showed the presence of pure rac-CH$_2$ (3-t-Bu-Ind)$_2$ZrCl$_2$ (65.7% yield). $^1$H NMR (CD$_2$Cl$_2$, δ, ppm): 1.37 (s, 18H, t-Bu); 4.79 (s, CH$_2$, 2H); 5.78 (s, Cp-H, 2H); 7.06–7.79 (m, 8H).

The solubility of rac-CH$_2$(3-t-Bu-Ind)$_2$ZrCl$_2$ in toluene was about 50 g/l.

The residue on the frit (red violet solid) was dried and the $^1$H-NMR analysis showed that it contained the two isomers meso:rac=93:7. Said residue was washed with tetrahydrofuran and dried again, thus giving a final product (1.2 g of red violet powder) consisting of pure meso CH$_2$(3-t-Bu-Ind)$_2$ZrCl$_2$ (24.2% yield).

$^1$H NMR (CD$_2$Cl$_2$, δ, ppm): 1.48 (s, 18 H, t-Bu); 4.77 (d, J=14.09, 1H, CH); 5.09 (d, J=14.09, 1H, CH); 5.86 (s, 2H, Cp-H); 6.87–7.67(m, 8H).

Synthesis 2 rac-Methylene-bis(3-t-butyl-1-indenyl)hafnium dichloride 4.14 g of crude bis(1-tert-butyl-3-indenyl)methane (78.3% of pure product, 9.1 mmol), obtained as described in synthesis 1, were dissolved in 80 mL Et$_2$O, in a 100 mL Schlenk tube, and the solution was cooled to −20° C. 9.8 mL of 2.5 M BuLi in hexane (24.5 mmol) were added dropwise, over 5 minutes, under stirring. The solution was allowed to warm to room temperature and stirred for 5 hours. An increasing turbidity developed with final formation of an orange suspension. 3.72 g of HfCl$_4$ (99.99% Hf 11.62 mmol) were slurried in 80 mL pentane. The two mixtures were both cooled to −78° C. and the Li salt solution in Et$_2$O was quickly added to the HfCl$_4$ slurry in pentane. The cooling bath was removed and after 2 hours the color of the slurry changed from yellow to orange. The reaction mixture was stirred overnight at room temperature and then was brought to dryness under reduced pressure. The orange powder was slurried in 80 mL of pentane, stirred for 15 minutes and transferred into a filtration apparatus equipped with side arm (to allow solvent refluxing) connecting the system above and below the frit, a receiving flask on the bottom and bubble condenser on the top. The filtered 80 mL of pentane solution were separated and pentane removed to dryness; a sticky product was obtained which was washed with 4 mL Et$_2$O, then dried again to yield 0.4 g of orange powder, which was pure rac-CH$_2$(3-$^t$Bu-1-Ind)$_2$HfCl$_2$.

$^1$H NMR (CD$_2$Cl$_2$, δ, ppm): 1.37 (s, $^t$Bu, 18H); 4.78 (s, CH$_2$, 2H); 5.72 (s, 2H, Cp-H); 7.07–7.12 (t, Ar, 2H); 7.25–7.35 (t, Ar, 2H); 7.50–7.57 (d, 2H); 7.7–7.8 (d, 2H).

The remaining solid was extracted with refluxing CH$_2$Cl$_2$ for about 3 hours. The filtrate was evaporated to dryness under reduced pressure to give a light orange powder which was then washed with pentane to give 3.4 g of a 75/25 rac/meso mixture, including some polymeric material.

Synthesis 3 rac-Methylene-bis(3-t-butyl-1-indenyl)titanium dichloride 6.1 g of pure bis(1-tert-butyl-3-indenyl)methane (16.0 mmol), obtained as described in synthesis 1, were dissolved in 120 mL Et$_2$O, in a 250 mL Schlenk tube, and the solution was cooled to −20° C. 14.4 mL of 2.5 M BuLi in hexane (36.0 mmol) were added dropwise, over 10 minutes, under stirring. The solution was allowed to warm to room temperature and stirred for 5 hours. An increasing turbidity developed with final formation of an orange suspension. 1.88 mL of TiCl$_4$ (17.0 mmol) were dissolved in 120 mL pentane. The two mixtures were both cooled to −80° C. and the Li salt solution in Et$_2$O were quickly added to the TiCl$_4$ in pentane. The cooling bath was removed and the reaction mixture was maintained under stirring overnight, at room temperature, to give a dark brown mixture, which was then brought to dryness under reduced pressure. The dark brown powder was slurried in 100 mL of pentane and transferred into a filtration apparatus equipped with side arm (to allow solvent refluxing) connecting the system above and below the frit, a receiving flask on the bottom and bubble condenser on the top. The filtered 100 mL of pentane solution were separated and pentane removed to dryness, to yield 3 g of a dark solid, which was washed with 20 mL Et$_2$O, and then dried again to give 0.52 g of pure rac-CH$_2$(3-$^t$Bu-1-Ind)$_2$TiCl$_2$.

$^1$H NMR (CD$_2$Cl$_2$, δ, ppm): 1.38 (s, $^t$Bu, 18H); 4.91 (s, CH$_2$, 2H); 5.25 (s, 2H, Cp-H); 7.02–7.12 (t, Ar, 2H); 7.3–7.5 (d+t, Ar, 4H); 7.70–7.75 (d, 2H).

The remaining solid was extracted with refluxing CH$_2$Cl$_2$ for about 3 hours. The filtrate was evaporated to dryness under reduced pressure to give 5.0 g of a dark powder which, due to its low purity, was further washed with Et$_2$O (25 mL) to give 0.54 g of pure product. The combined yield was 14%.

Synthesis 4 rac-Methylene-bis(3-t-butyl-1-indenyl)zirconium dimethyl 3.06 ml of a solution of methyllithium 1.6 M (4.9 mmoles) in Et$_2$O were added, at the temperature of −78° C., over a period of about 10 minutes, to a solution containing 1.2 g (9.23 mmoles) of rac-CH$_2$(3-tert-butyl-1-indenyl)$_2$ZrCl$_2$, obtained as reported in synthesis 1, in 50 mL of Et$_2$O. The reaction mixture was stirred, at room temperature, for 24 hours, and a dark brown solution was finally obtained. The reaction mixture was then brought to dryness under reduced pressure, thus isolating a brown solid, which was extracted with pentane; the filtrate was evaporated to dryness under reduced pressure, thus giving 0.56 g (51% yield) of a pale yellow solid, which was identified at the $^1$H-NMR analysis as chemically pure rac-CH$_2$(3-tert-butyl-1-indenyl)$_2$ZrMe$_2$.

$^1$H NMR (d, ppm, C$_6$D$_6$): CH$_3$, s, −0.82, 6H; $^t$Bu, s, 1.39, 18H; —CH$_2$—, s, 3.84, 2H; Cp-H, s, 5.49, 2H; Ar, t,d,t, 6.7–7.2, 6H; d, 7.7–7.8, 2H.

Synthesis 5 rac-Methylene-bis(4,7-dimethylindenyl)zirconium dichloride (a) Synthesis of bis(4,7-dimethylindenyl)methane Paraformaldehyde (2.08 g, 69.4 mmol) was added to a mixture of 4,7-dimethylindene (25.0 g, 174 mmol) and EtONa (5.9 g, 87 mmol) in DMSO (200 mL) at 25° C. After stirring at room temperature for 12 hours, the reaction mixture was heated at 65° C. for 8 hours. It was then cooled to room temperature and a solution of HCl (1 M, 400 mL) was added. The mixture was extracted with CH$_2$Cl$_2$ (400 mL); the organic phases were combined, washed with a saturated solution of NaCl and then with water, dried with MgSO$_4$, filtered and finally concentrated to yield a brown viscous liquid. GC analysis showed only the final product and the starting material, no fulvene derivative being detectable. Precipitation occurred when the brown liquid was added into pentane (100 mL). Bis(4,7-dimethylindenyl)methane was obtained as a yellow solid after filtering and washing with pentane and EtOH, with a yield of 33% (6.8 g).

$^1$H NMR (CDCl$_3$, d, ppm): 6.85–7.05 (m, 4 H), 6.35 (s, 2 H), 4.20 (s, 2 H), 3.2 (s, 4 H), 2.55 (s, 6 H), 2.35 (s, 6 H).

(b) Synthesis of methylene-bis(4,7-dimethylindenyl)zirconium dichloride

A suspension of bis(4,7-dimethyl-indenyl)methane (2 g, 6.7 mmol), obtained as reported above, in THF (30 mL) was added via cannula to a stirred suspension of KH (0.6 g, 15 mmol) in THF (35 mL). After hydrogen evolution had ceased (2 hours), the resulting brownish solution was separated from excess KH. This solution and a solution of ZrCl$_4$(THF)$_2$ (2.5 g, 6.7 mmol) in THF (65 mL) were both added dropwise, via dropping funnels, to a flask containing THF (30 mL), under vigorous stirring, over 4 hours. At the end of the addition, the mixture was stirred overnight. A brick-red solution and a precipitate formed. After concentrating in vacuum to about 4 mL, 10 mL of Et$_2$O were added; the suspension was filtered and the residue was dried in vacuum, thus obtaining a brown powder. Said powder was extracted with refluxing CH$_2$Cl$_2$ until the washing was colorless. The CH$_2$Cl$_2$ solution was concentrated to 7 mL and cooled to −20° C. overnight. By filtration were isolated 0.715 g of methylene-bis(4,7-dimethylindenyl)zirconium dichloride as a red solid. $^1$H NMR analysis confirmed the formation of the pure racemic isomer.

$^1$H NMR (CDCl$_3$, δ, ppm): 7.00, 6.97 (d, 2H), 6.78, 6.74 (d, 2H), 6.66, 6.64 (d, 2H), 5.89, 5.87 (d, 2H), 5.09 (s, 2H), 2.76 (s, 6H), 2.30 (s, 6H).

Synthesis 6 rac-Methylene-bis(1-phenyl-5,7-dimethyl-indenyl)zirconium dichloride (a) Synthesis of 5,7-dimethylindan-1-one A mixture of 3-chloropropionyl chloride (118.9 g, 0.94 mol) and p-xylene (100 g, 0.94 mol) in CH$_2$Cl$_2$ (200 mL) was added dropwise to AlCl$_3$ (283 g, 2.12 mol), at 0° C. The reaction mixture was then stirred at room temperature, for 12 hours. The obtained slurry was poured into a flask containing 1.5 kg of ice. The product was extracted with Et$_2$O (2×800 mL); the organic layers were combined, washed with a saturated solution of NaHCO$_3$ (800 mL) and then water (800 mL), dried over MgSO$_4$, filtered and concentrated to obtain 175 g of a viscous liquid. The product was used in the next step without further purification.

400 mL of concentrated sulfuric acid were added dropwise to the product obtained as reported above. The solution was heated at 65° C. for 5 hours. The reaction mixture was then cooled to room temperature and slowly poured into a flask containing 2 kg of ice. The mixture was extracted with CH$_2$Cl$_2$ (2×1000 mL); the organic phases were combined, washed with a saturated solution of NaHCO$_3$ and then water, dried over MgSO$_4$, filtered and finally concentrated. 5,7-Dimethylindan-1-one was isolated by crystallization from hexane (71.4 g, 47% yield).

$^1$H NMR (CDCl$_3$, d, ppm): 7.1 (s, 1 H), 6.9 (s, 1 H), 2.9–3.1 (m, 2 H), 2.6–2.7 (m, 2 H), 2.55 (s, 3 H), 2.4 (s, 3 H).

(b) Synthesis of 3-phenyl-4,6-dimethylindene 5,7-Dimethylindan-1-one (13.5 g, 84.4 mmol), obtained as reported above, in THF (20 mL) was added dropwise to a solution of PhMgBr (3.0 M in Et$_2$O, 63 mL, 188 mmol), at 0° C. The reaction mixture was stirred at room temperature overnight and then quenched with a saturated solution of ammonium chloride (600 mL). The mixture was extracted with Et$_2$O (2×500 mL); the organic phases were combined, dried over MgSO$_4$, and concentrated to yield a viscous liquid. The product was used in the next step without further purification.

A mixture of the above product (16 g) and p-toluenesulfonic acid monohydrate (2.6 g) in benzene was heated at reflux for 3 hours. The mixture was cooled to room temperature and then treated with a saturated solution of NaHCO$_3$. The organic layer was washed with water, dried over MgSO$_4$, concentrated and vacuum distilled to yield 3-phenyl-4,6-dimethylindene (b.p. 120° C. at 0.5 mmHg, 11.6 g, 78%).

(c) Synthesis of bis(1-phenyl-5,7-dimethyl-indenyl)methane

Paraformaldehyde (68 mg, 2.27 mmol) was added to a mixture of 3-phenyl-4,6-dimethylindene (1.0 g, 4.55 mmol), obtained as reported above, and EtONa (0.15 g, 2.27 mmol) in DMSO (15 mL) at 25° C. After stirring at room temperature for 4 hours, the reaction mixture was treated with a solution of HCl (1 M, 100 mL). The mixture was extracted with CH$_2$Cl$_2$ (2×100 mL); organic phases were combined, washed with a saturated solution of NaCl and then with water, dried with MgSO$_4$, filtered and finally concentrated to yield a brown viscous liquid. Precipitation in MeOH and filtration yielded 0.45 g of bis(1-phenyl-5,7-dimethyl-indenyl)methane as a solid (yield 44%).

$^1$H NMR (CDCl$_3$, d, ppm): 7.7 (m, 14 H), 6.25 (s, 2 H), 4.5 (s, 2 H), 3.8 (s, 2 H), 2.35 (s, 6 H), 2.0 (s, 6 H).

(d) Synthesis of methylene-bis(3-phenyl-4,6-dimethyl-indenyl)zirconium dichloride 2.5 g of bis(1-phenyl-5,7-dimethyl-indenyl)methane (5.53 mmol), obtained as reported above, were dissolved in 25 mL THF and slowly added to a stirred suspension of 0.5 g KH (12.5 mmol) in 10 mL THF, in a 50 mL Schlenk tube. Evolution of H$_2$ ceased after 2 hours and the resulting brownish solution was separated from excess KH. This solution and a solution of ZrCl$_4$(THF)$_2$ (2.08 g, 5.53 mmol) in THF (35 mL) were both added dropwise, via dropping funnels, to a 250 mL flask containing THF (35 mL), under vigorous stirring, over 6 hours. At the end of the addition, the mixture was stirred overnight at room temperature. A red cloudy solution was obtained. After drying under reduced pressure, the residue was extracted with refluxing CH$_2$Cl$_2$ until the washing was colorless. The CH$_2$Cl$_2$ solution was brought to dryness and the residue extracted with refluxing pentane, for 10 hours. The pentane solution was concentrated to 10 mL. The precipitated product was filtered off and dried in vacuum to yield 0.4 g of red rac-CH$_2$(3-phenyl-4,6-dimethyl-1-Ind)$_2$ZrCl$_2$, free from the meso isomer $^1$H NMR (CDCl$_3$, δ, ppm): 2.09 (s, CH$_3$); 2.64 (s, CH$_3$); 4.78 (s, 2H, CH$_2$); 5.80 (s, 2H, Cp-H); 6.85 (s, 2H); 7.04 (s, 2H); 7.30 (m, 6H); 7.44 (m, 4H).

Synthesis 7 rac-Methylene-bis(2-methyl-1-indenyl)zirconium dichloride (a) Synthesis of bis(2-methyl-1-indenyl)methane 3.06 g of NaOEt (45.0 mmol), dissolved in 600 mL of DMF, and 30.00 g of 2-methylindene (224.9 mmol) were introduced at room temperature in this order in a three neck, 1000 mL flask with stirring bar. 9.10 mL of aqueous formalin (37%, 112.1 mmol) were added dropwise: a mildly exothermic reaction was observed and the solution turned to dark brown. At the end of the addition, the reaction mixture was stirred for 2 hours at room temperature. The reaction was then quenched by pouring the mixture on ice and NH$_4$Cl. The organic product was extracted with Et$_2$O (3×200 ml) and the water layer was washed with Et$_2$O; the organic layers were combined, washed with water to eliminate the remaining DMF, then dried over MgSO$_4$, filtered and finally concentrated, thus obtaining 30.54 g of orange-brown oil. Said oil was washed with 100 ml pentane and dried again. The GC analysis showed that the final product (12.02 g of white powder) was crude bis(2-methyl-indenyl)methane, and more specifically: bis(2-methyl-lindenyl)methane 85.3% and trimer 12.1%.

$^1$H NMR (CDCl$_3$, δ, ppm): 2.15 (s, 6H, CH$_3$); 3.31 (s, CH$_2$, 4H); 3.74 (s, 2H, CH$_2$ bridge); 7.10–7.36 (m, 8H). GC-MS: m/z (%)=272 (M$^+$), 143 (M$^+$-C$_{10}$H$_9$), 128 (M$^+$-C$_{11}$H$_{12}$), 115 (C$_9$H$_7^+$).

(b) Synthesis of rac-methylene-bis(2-methyl-1-indnyl) ZrCl$_2$.

2.11 g of raw bis(2-methyl-1-indenyl)methane (90.6% by GC, 7.8 mmol) were dissolved in 50 ml Et$_2$O in a 100 ml Schlenk tube, and the solution was cooled to −70° C. 10.2 ml of 1.6 M BuLi in hexane (16.3 mmol) were added dropwise under stirring. The obtained solution was allowed to warm to room temperature and stirred for 3 hours. An increasing turbidity developed with final formation of a light yellow suspension. 1.80 g of ZrCl$_4$ (7.7 mmol) were slurried in 30 ml of pentane. The two mixtures were both cooled to −70° C. and the Li salt solution in Et$_2$O was quickly added to the ZrCl$_4$ slurry in pentane: instantly, the slurry turned from yellow to orange-red The cooling bath was removed. The reaction mixture was maintained under stirring overnight, at room temperature, and the colour of the suspension turned to orange. After filtration (the filtrate was eliminated), the residue was extracted with toluene and the obtained filtrate was evaporated to dryness, under reduced pressure, to give 1.30 g of an orange powder. The $^1$H-NMR analysis showed the presence of rac/meso CH$_2$(2-Me-1-Ind)$_2$ZrCl$_2$=75/25 (38.5% yield).

Synthesis 8 rac-Methylene-bis(3-trimethylsilyl-1-indenyl) zirconium dichloride (a) Synthesis of bis(1-trimethylsilyl-3-indenyl)methane 9.56 g of bis(1-indenyl)methane (39,1 mmol), obtained as reported in Synthesis 10, were dissolved in 70 ml Et$_2$O in a 250 ml Schlenk tube, and the solution cooled to −78° C. 33.0 ml of 2.5 M BuLi in hexane (82.5 mmol) were added dropwise, over 30 minutes under stirring. The obtained solution was allowed to warm to room temperature and then stirred for 3 hours, thus obtaining a brown dark, lightly cloudy solution. 10.5 ml of chlorotrimethylsilane (82.7 mmol) were dissolved in 50 ml Et$_2$O. The two mixtures were both cooled to −78° C. and the Li salt solution in Et$_2$O was added, over 20 minutes, to the chlorotrimethylsilane solution in Et$_2$O; the color of the solution turned from brown to maroon. The cooling bath was removed and the reaction mixture was stirred overnight at room temperature. After 20 hours, the solution, lightly clearer, was quenched with a few ml of MeOH, filtered and concentrated, thus giving 11.28 g of bis(1-trimethylsilyl-3-indenyl)methane as a brown dark oil (74.2% yield, meso/rac=1/1).

$^1$H NMR (CDCl$_3$, δ, ppm): −0.04 to −0.03 (s, 18H, CH$_3$); 3.35–3.45 (m, 2H, CH or CH$_2$ bridge); 3.93–4.00 (bs, 2H, CH$_2$ bridge or CH); 6.30–6.40 (m, 2H, Cp-H); 7.10–7.50 (m, 8H).

(b) Synthesis of CH$_2$(3-Me$_3$Si-Ind)$_2$ZrCl$_2$ 4.90 g of bis(1-trimethylsilyl-3-indenyl)methane (12.6 mmol), obtained as reported above, were dissolved in 70 ml Et$_2$O in a 250 ml Schlenk tube, and the solution was cooled to −70° C. 10.6 ml of 2.5 M BuLi in hexane (26.5 mmol)

were added dropwise under stirring. The solution was allowed to warm to room temperature and stirred for 3 hours. An increasing turbidity developed with the final formation of a brown dark suspension. 2.94 g of $ZrCl_4$ (12.6 mmol) were slurried in 50 ml of pentane. The two mixtures were both cooled to −70° C. and the Li salt solution in $Et_2O$ was quickly added to the $ZrCl_4$ slurry in pentane; then the cooling bath was removed. The reaction mixture was maintained under stirring overnight at room temperature and the color of the suspension turned to maroon. After filtration, the residue was concentrated and then extracted with toluene to give a pink-red powder. The $^1$H-NMR analysis showed the presence of meso/rac $CH_2(3-Me_3Si-1-Ind)_2ZrCl_2=75/25$. The filtrate was dried to give a brown dark sticky solid and pentane was added; the obtained mixture was stirred at room temperature for 1 hour and then filtered. The residue was finally dried to give 1.87 g of an orange powder. The $^1$H-NMR analysis showed the presence of rac/meso $CH_2(3-Me_3Si-1-Ind)_2ZrCl_2=81/19$ (27.0% yield).

$^1$H NMR ($CD_2Cl_2$, δ, ppm): 0.22 (s, 6H, $CH_3$); 0.34 (s, 6H, $CH_3$); 4.79 (s, $CH_2$ bridge, 2H); 4.93 (q, $CH_2$ bridge, 2H); 6.47 (s, Cp-H, 2H); 6.57 (s, Cp-H, 2H); 7.06–7.72 (m, 16K).

Synthesis 9 rac-Methylene-bis(2-methyl-3-trimethylsilyl-1-indenyl)zirconium dichloride (a) Synthesis of bis(2-methyl-3-trimethylsilyl-1-indenyl)methane 6.32 g of bis(2-methyl-1-indenyl)methane (23.2 mmol) were dissolved in 70 ml $Et_2O$ in a 250 ml Schlenk tube, and the white suspension was cooled to −50° C. 19.5 ml of 2.5 M BuLi in hexane (48.8 mmol) were added dropwise over 20 minutes under stirring. The suspension was allowed to warm to room temperature and stirred for 3 hours. The final suspension was light yellow. 6.2 ml of chlorotrimethylsilane (48.8 mmol) were dissolved in 50 ml $Et_2O$. The two mixtures were both cooled to −50° C. and the Li salt suspension in $Et_2O$ was added to the chlorotrimethylsilane solution in $Et_2O$. The cooling bath was removed and the reaction mixture was stirred overnight at room temperature. Then the reaction mixture, colored in yellow, was quenched with a few ml of MeOH, filtered and concentrated, thus giving 9.36 g of an brown and viscous liquid (96.8% yield).

$^1$H NMR ($CDCl_3$, δ, ppm): −0.06,−0.04 (s, 9H, Si($CH_3)_3$); 2.21,2.23 (s, 3H, $CH_3$); 3.32 (s, 2H, CH or $CH_2$ bridge); 3.83 (s, 2H, $CH_2$ bridge or CH); 7.05–7.36 (m, 8H).

(b) Synthesis of rac-methylene-bis(2-methyl-3-trimethylsilyl-1-indenyl)$ZrCl_2$.

9.36 g of bis(2-methyl-3-trimethylsilyl-1-indenyl)methane (22.5 mmol), prepared as described above, were dissolved in 80 ml $Et_2O$ in a 250 ml Schlenk tube, and the solution was cooled to −20° C. 18.9 ml of 2.5 M BuLi in hexane (47.2 mmol) were added dropwise under stirring. The solution was allowed to warm to room temperature and maintained under stirring for 3 hours. The color of the solution turned from brown to orange. 5.24 g of $ZrCl_4$ (22.5 mmol) were slurried in 50 ml of pentane. The two mixtures were both cooled to −70° C. and the Li salt solution in $Et_2O$ was quickly added to the $ZrCl_4$ slurry in pentane; then the cooling bath was removed.

The reaction mixture was stirred overnight at room temperature with final formation of a brick-red suspension. After filtration, the filtrate was dried to give a brown sticky solid (eliminated); the residue was concentrated and then extracted with toluene, thus giving 9.18 g of a maroon powder. The $^1$H-NMR analysis showed the presence of rac/meso $CH_2(2-Me-3-Me_3Si-1-Ind)_2ZrCl_2=95/5$ (70.7% yield).

$^1$H NMR ($CD_2Cl_2$, δ, ppm): 0.32, 0.42 (s, 9H, Si($CH_3)_3$); 2.24,2.49 (s, 6H, $CH_3$); 4.93 (s, $CH_2$ bridge, 2H); 5.10 (d, 2H, $CH_2$ bridge); 7.04–7.72 (m, 16H).

Synthesis 10 rac-Methylene-bis(1-indenyl)zirconium dichloride (a) Synthesis of bis(1-indenyl)methane 3.5 g of formalin (37% solution, 43.1 mmol) was added to a mixture of 10.0 g of indene (86.2 mmol) and 2.9 g of EtONa (43.1 mmol) in 100 mL of DMF. The reaction mixture was stirred at room temperature for 12 hours. A solution of HCl (1 M, 50 mL) was added. The mixture was extracted with $CH_2Cl_2$ (2×100 mL) and the organic phases combined, washed with a saturated solution of NaCl and then with water, dried over $MgSO_4$, filtered and finally concentrated to yield bis(1-indenyl)methane as a viscous brown liquid (89% yield by GC). Vacuum distillation yielded the pure product as a yellow viscous oil (b.p. 160–180° C. at 1.2 mmHg, 3.65 g, 35% yield), which can be recrystallized from pentane.

$^1$H NMR ($CDCl_3$, d, ppm): 7.10–7.60 (m, 8 H), 6.25 (s, 2 H), 3.85 (s, 2H), 3.40 (s, 4 H).

(b) Synthesis of methylene-bis(1-indenyl)zirconium dichloride 2.135 g of bis(1-indenyl)methane (8.75 mmol), obtained as reported above, were dissolved in 30 mL THF and slowly added to a stirred suspension of 0.8 g KH (19.5 mmol) in 50 mL THF, in a 100 mL Schlenk tube. Evolution of $H_2$ ceased after 1 hour and 30 min, and the resulting brownish solution was separated from excess KH. This solution and a solution of $ZrCl_4(THF)_2$ (3.3 g, 8.75 mmol) in THF (80 mL) were both added dropwise via dropping funnels to a 250 mL flask containing THF (20 mL), under vigorous stirring, over 5.5 hours. At the end of the addition, the mixture was stirred overnight at room temperature. A yellow-orange solution and a precipitate formed. After concentrating of the suspension under reduced pressure to about 10 mL, 10 mL of $Et_2O$ were added; the suspension was filtered and the residue was dried in vacuum and finally extracted with refluxing $CH_2Cl_2$, until the washing was colorless (2 hours). The $CH_2Cl_2$ solution (part of the product precipitated during extraction) was concentrated to yield 2.135 g of a red solid product. Said product was washed with $Et_2O$ (3×5 mL), with 2 mL $CH_2Cl_2$ and again with $Et_2O$, to give 1.06 g of methylene-bis(1-indenyl)zirconium dichloride with some organic impurities. Crystallization from toluene yielded 0.32 g of red-orange rac-$CH_2(1-Ind)_2ZrCl_2$, free from the meso isomer. $^1$H NMR ($CD_2Cl_2$, δ, ppm): 4.87 (s, 2H, $CH_2$); 6.02–6.04 (d, 2H); 6.59–6.61 (d, 2H); 7.1–7.7 (3m, 8H).

POLYMERIZATION TESTS

Methylalumoxane (MAO)

A commercial (Witco) 10% toluene solution was dried in vacuum until a solid, glassy material was obtained, which was finely crushed and further treated in vacuum until all volatiles were removed (4–6 hours, 0.1 mmHg, 50° C.) to leave a white, free-flowing powder.

Tris(2,4,4-trimethyl-pentyl)aluminum (TIOA)

A commercial (Witco) sample was used diluted to a 1 M solution in the indicated solvent.

Tris (2-methyl-propyl)aluminum (TIBA)

The commercial product was purchased from Witco and used as a 1M solution in hexane.

$PhNMe_2H/B(C_6F_5)_4$

The commercial product was purchased from Asahi Glass Co.

EXAMPLES 1–6
Ethylene Polymerization

A 200 ml glass autoclave, provided with magnetic stirrer, temperature indicator and feeding line for ethylene, was purified and fluxed with ethylene at 35° C. At room temperature 90 ml of hexane were introduced. The catalytic system was separately prepared in 10 ml of hexane by consecutively introducing the cocatalyst reported in Table 1 and, after 5 minutes of stirring, the bridged metallocene compound reported in Table 1, dissolved in the lowest possible amount of toluene. After 5 minutes stirring, the solution was introduced into the autoclave under ethylene flow; the reactor was closed; the temperature was risen to 80° C. and pressurized to 4.6 barg. The total pressure was kept constant by feeding ethylene. After the polymerization time reported in Table 1, the polymerization was stopped by cooling, degassing the reactor and by the introduction of 1 ml of methanol. The product was washed with acidic methanol, than with methanol and finally dried in oven at 60° C., under vacuum. The yields of the polymerization reactions as well as the characteristics of the obtained polymers are reported in Table 1.

EXAMPLE 7
Ethylene/1-hexene Copolymerization

Example 1 was repeated with the following differences: instead of the 90 ml of hexane, 80 ml of heptane and 10 ml of 1-hexene were introduced in the autoclave; the catalytic system was prepared in 10 mL of heptane instead of hexane; the polymerization was run at 70° C. and 4.5 barg and it was stopped after 10 minutes. The yield was 1.0 g corresponding to an activity of 339.9 Kg/mmol$_{zr}$.h. The intrinsic viscosity of the copolymer was 2.59 dL/g. The amount of 1-hexene units in the copolymer was 13.7% by weight.

EXAMPLE 8
Ethylene/propylene Copolymerization

The copolymerization was carried out by continuously supplying the monomer mixture at a constant flow rate in a 250 mL glass reactor equipped with stirring and a thermometer. The cocatalyst was prepared by dissolving 3.45 mL of TIOA (1 M in hexane) in 5 mL of toluene, then adding 0.031 mL of water and then stirring the solution for 10 minutes. The cocatalyst was then added to the nitrogen purged reactor containing 95 mL of toluene. The reactor was put into a thermostatted bath and, when the reaction temperature of 50° C. was reached, a mixture of ethylene and propylene containing 60% wt of ethylene was supplied continuously, at a total pressure of 80 mmHg and a flow rate of 80 L/h. 1.8 mg (3.45 mmol) of rac-methylene-bis(3-t-butyl-1-indenyl) zirconium dichloride, dissolved in 5 mL of toluene, were added to start the polymerization. After 15 minutes, the polymerization reaction was stopped by adding 1 mL of methanol and the copolymer was coagulated in acidulated methanol, then filtered and dried under vacuum. The yield was 2.42 g. The intrinsic viscosity of the copolymer was 2.9 dL/g. The amount of propylene units in the copolymer was 18.3% by weight.

EXAMPLES 9–10, 15–23 and 29–33, and COMPARATIVE EXAMPLES 11–14 and 24–28
Propylene Polymerization 200 g of propylene were charged in a 1-L jacketed stainless-steel autoclave, equipped with magnetically driven stirrer and a 35-mL stainless-steel vial, connected to a thermostat for temperature control; the autoclave had been previously purified by washing with a TIBA solution in hexanes, dried at 50° C. in a stream of propylene and finally cooled to room temperature (in examples 16–23 and 29–33, a 4.25-L autoclave was used and propylene was charged therein, in order to have a volume of 2 L of liquid propylene, at the polymerization temperature). When used, hydrogen was charged in the reactor at room temperature, before charging liquid propylene. The autoclave was then thermostatted at the polymerization temperature indicated in Table 2. The catalyst mixture was prepared by adding the amount of the racemic zirconocene dichloride indicated in Table 2 to a MAO solution in toluene, thus obtaining a solution which was stirred for 10 minutes at room temperature and then injected into the autoclave by means of nitrogen pressure, through the stainless-steel vial, at the polymerization temperature. The polymerization was carried out at constant temperature for 1 hour and then quenched with carbon monoxide. After venting the unreacted monomer and cooling the reactor to room temperature, the polymer was dried under reduced pressure at 60° C. The polymerization data are reported in Table 2. The data relating to the characterization of the obtained polymers are reported in Table 3.

TABLE 1

| | | | Ethylene polymerization | | | | | |
|---|---|---|---|---|---|---|---|---|
| Ex. | rac-zirconocene dichloride | Zr (mg) | Cocatalyst | Cocat. (mmol) | Time (min) | yield (g) | activity (Kg/g$_{Zr}$.h) | I.V. (dL/g) |
| 1 | CH$_2$(3-tBuInd)$_2$ | 0.1 | MAO | 0.21 | 8 | 2.12 | 900.8 | 6.5 |
| 2 | " | 0.1 | TIOA/H$_2$O* | 0.97 | 6 | 1.16 | 657.2 | 7.9 |
| 3 | " | 0.3 | MAO | 0.12 | 3 | 1.66 | 629.0 | n.d. |
| 4 | " | 0.3 | $^-$B(C$_6$F$_5$)$_4$ | ** | 3 | 0.84 | 317.3 | 7.1 |
| 5 | CH$_2$(3-TMS-Ind)$_2$ | 0.1 | MAO | 0 | 6 | 2.17 | 1088.2 | 2.2 |
| 6 | CH$_2$(3-TMS-2-Me-Ind)$_2$ | 0.1 | MAO | 0 | 10 | 1.84 | 698.3 | 3.2 |

*To 0.97 mmol of TIOA (1M in heptane) were added 0.46 mmol of H$_2$O;

**PhNMe$_2$H/B(C$_6$F$_5$)$_4$ was used in association with 0.31 mmol TIBA, at a molar ratio B/Zr=

TABLE 2

Propylene polymerization

| Example | rac-zirconocene dichloride | Zr (mg) | Al/Zr (mol) | $H_2$ (mL) | T (°C.) | yield (g) | activity (Kg/$g_{cat}$·h) |
|---|---|---|---|---|---|---|---|
| 9 | $CH_2(4,7\text{-}Me_2Ind)_2ZrCl_2$ | 1.1 | 2000 | 0 | 50 | 58.6 | 51 |
| 10 | " | 0.2 | 5000 | 0 | 70 | 45.8 | 229 |
| Comp. 11 | $CH_2(Ind)_2ZrCl_2$ | 0.5 | 4000 | 0 | 50 | 76.6 | 153 |
| Comp. 12 | " | 0.2 | 10000 | 0 | 70 | 17.6 | 88 |
| Comp. 13 | $C_2H_4(4,7\text{-}Me_2Ind)_2ZrCl_2$ | 1.0 | 2000 | 0 | 50 | 142.7 | 143 |
| Comp. 14 | " | 0.5 | 2000 | 0 | 70 | 20.8 | 42 |
| 15 | $CH_2(3\text{-}Ph\text{-}4,6\text{-}Me_2Ind)_2ZrCl_2$ | 1.0 | 5000 | 0 | 50 | 77.6 | 127 |
| 16 | $CH_2(3\text{-}tBuInd)_2ZrCl_2$ | 2.0 | 1000 | 0 | 30 | 64.7 | 32 |
| 17 | " | 2.0 | 1000 | 0 | 40 | 105.7 | 53 |
| 18 | " | 2.0 | 1000 | 0 | 60 | 176.7 | 88 |
| 19 | " | 1.5 | 1000 | 0 | 70 | 138.8 | 92 |
| 20 | " | 1.5 | 3000 | 0 | 60 | 209.0 | 139 |
| 21 | " | 2.0 | 500 | 0 | 60 | 123.9 | 62 |
| 22 | " | 2.0 | 500 | 50 | 60 | 196.0 | 98 |
| 23 | " | 2.0 | 500 | 100 | 60 | 186.9 | 93 |
| Comp. 24 | $Me_2C(3\text{-}tBuInd)_2ZrCl_2$ | 0.2 | 8000 | 0 | 30 | 25.3 | 126 |
| Comp. 25 | " | 0.2 | 8000 | 0 | 40 | 41.3 | 206 |
| Comp. 26 | " | 0.1 | 8000 | 0 | 50 | 22.9 | 229 |
| Comp. 27 | " | 0.2 | 8000 | 0 | 60 | 59.0 | 295 |
| Comp. 28 | " | 0.1 | 8000 | 0 | 70 | 20.2 | 202 |
| 29 | $CH_2(3\text{-}tBuInd)_2ZrCl_2$ | 6 | 250 | 0 | 60 | 300 | 50 |
| 30 | " | 4 | 200 | 0 | 60 | 120 | 30 |
| 31 | $CH_2(3\text{-}tBuInd)_2ZrMe_2$ | 4 | 200 | 0 | 60 | 200 | 50 |
| 32 | " | 4 | 200 | 70 | 60 | 208 | 52 |
| 33 | " | 4 | 200* | 0 | 60 | 300 | 75 |

*Dried MAO was used (60° C., 6 hours, 1 mmHg)

TABLE 3

Propylene polymerization

| Example | rac-zirconocene dichloride | I.V. (dL/g) | Mv | Mn | mmmm (%) | R.I. (%) | Tm (°C.) |
|---|---|---|---|---|---|---|---|
| 9 | $CH_2(4,7\text{-}Me_2Ind)_2ZrCl_2$ | n.m. | n.d. | 2000 | 85.9 | 0.82 | 122 |
| 10 | " | n.m. | n.d. | 2350 | 84.4 | 1.12 | n.d. |
| Comp. 11 | $CH_2(Ind)_2ZrCl_2$ | 0.11 | n.d. | 3200 | 71.4 | 0.47 | n.d. |
| Comp. 12 | " | 0.09 | n.d. | 2800 | n.d. | n.d | n.d. |
| Comp. 13 | $C_2H_4(4,7\text{-}Me_2Ind)_2ZrCl_2$ | 0.12 | n.d. | 3400 | 92.3 | 1.86 | 131 |
| Comp. 14 | " | 0.14 | n.d. | 2800 | 90.7 | 2.4 | n.d. |
| 15 | $CH_2(3\text{-}Ph\text{-}4,6\text{-}Me_2Ind)_2ZrCl_2$ | 0.2 | n.d. | n.d. | n.d. | n.d. | n.d. |
| 16 | $CH_2(3\text{-}tBuInd)_2ZrCl_2$ | 3.92 | 662600 | n.d. | 97.8 | 0 | 163 |
| 17 | " | 2.32 | 326200 | n.d. | 98.2 | 0 | 160 |
| 18 | " | 1.03 | 108900 | n.d. | 96.4 | 0 | 156 |
| 19 | " | 0.79 | 76100 | n.d. | 97.0 | 0 | 154 |
| 20 | " | 0.84 | 82600 | n.d. | n.d. | 0 | 159 |
| 21 | " | 1.07 | 114610 | n.d. | n.d. | 0 | 159 |
| 22 | " | 0.95 | 97600 | n.d. | n.d. | 0 | 158 |
| 23 | " | 0.90 | 90700 | n.d. | n.d. | 0 | 158 |
| Comp. 24 | $Me_2C(3\text{-}tBuInd)_2ZrCl_2$ | 1.74 | 210100 | n.d. | 91.3 | 0 | 157 |
| Comp. 25 | " | 1.18 | 130800 | n.d. | 93.1 | 0 | 156 |
| Comp. 26 | " | 0.89 | 89400 | n.d. | 94.8 | 0 | 152 |
| Comp. 27 | " | 0.53 | 44400 | n.d. | 95.5 | 0 | 148 |
| Comp. 28 | " | 0.33 | 23400 | n.d. | 96.8 | 0 | 140 |
| 29 | $CH_2(3\text{-}tBuInd)_2ZrCl_2$ | 0.87 | 87000 | n.d. | n.d. | 0 | n.d. |
| 30 | " | 1.05 | 112000 | n.d. | 96.5 | 0 | 157. |
| 31 | $CH_2(3\text{-}tBuInd)_2ZrMe_2$ | 1.05 | 112000 | n.d. | 97.0 | 0 | 157 |
| 32 | " | 1.06 | 113000 | n.d. | 97.0 | 0 | 158 |
| 33 | " | 1.20 | 134000 | n.d. | n.d. | 0 | n.d. | n.m. = not measurable
n.d. = not determined

What is claimed is:

1. A bridged metallocene compound having formula (III):

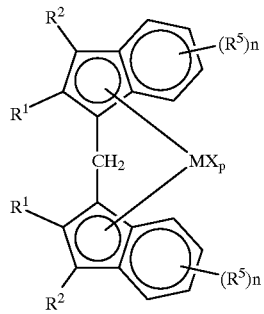

(III)

wherein $R^2$ is hydrogen; $R^1$ is selected from the group consisting of hydrogen atoms, linear or branched, saturated or unsaturated $C_1$–$C_{20}$-alkyl, $C_3$–$C_{20}$-cycloalkyl, $C_6$–$C_{20}$-aryl, $C_7$–$C_{20}$-alkylaryl and $C_7$–$C_{20}$-arylalkyl radicals, optionally containing Si or Ge atoms; M is a transition metal belonging to groups 3, 4, 5 or to the lanthanide or actinide groups of the Periodic Table of the Elements (new IUPAC notation);

the groups X, the same or different from each other, are monoanionic sigma ligands selected from the group consisting of hydrogen, halogen, —R, —OR, —OSO$_2$CF$_3$, —OCOR, —SR, —NR$_2$ and PR$_2$ groups, wherein the R substituents are $C_1$–$C_{20}$-alkyl, $C_3$–$C_{20}$-cycloalkyl, $C_2$–$C_{20}$-alkenyl, $C_6$–$C_{20}$-aryl, $C_7$–$C_{20}$-alkylaryl or $C_7$–$C_{20}$-arylalkyl, radicals, optionally containing Si or Ge atoms;

p is an integer ranging from 0 to 3, being equal to the oxidation state of the metal M minus two;

the $R^5$ substituents, the same or different from each other, are selected from the group consisting of linear or branched, saturated or unsaturated, $C_1$–$C_{20}$-alkyl, $C_3$–$C_{20}$-cycloalkyl, $C_6$–$C_{20}$-aryl, $C_7$–$C_{20}$-alkylaryl and $C_7$–$C_{20}$-arylalkyl radicals, optionally containing Si or Ge atoms, or two vicinal $R^5$ substituents form a ring having from 5 to 8 members; the $R^5$ groups in the positions 4 and 7 of the indenyl residues are different from hydrogen; and n is an integer ranging from 2 to 4.

2. The bridged metallocene compound according to claim 1, wherein the $R^5$ groups in the positions 4 and 7 of the indenyl residues are methyl, ethyl or phenyl.

3. The bridged metallocene compound according to claim 2, characterized by being rac-methylene-bis(4,7-dimethyl-indenyl)zirconium dichloride.

4. A process for the preparation of the metallocene compounds of formula (III), as reported in claim 1, comprising reacting a ligand of formula (IV):

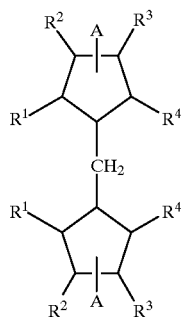

(IV)

wherein $R^1$, $R^2$, have the meaning reported in claim 1 the substituents $R^3$ and $R^4$ form a condensed, 6-membered, aromatic ring; the resulting indenyl moiety being substituted in the positions 4, 7 of by two $R^5$ groups wherein $R^5$ is defined in claim 1; wherein M is a transition metal belonging to groups 3, 4, 5 or to the lanthanide or actinide groups of the Periodic Table of the Elements (new IUPAC notation); the groups X, the same or different from each other, are monoanionic sigma ligands selected from the group consisting of hydrogen, halogen, —R, —OR, —OSO$_2$CF$_3$, —OCOR, —SR, —NR$_2$, and PR$_2$ groups, wherein the R substituents are $C_1$–$C_{20}$-alkyl, $C_3$–$C_{20}$-cycloalkyl, $C_2$–$C_{20}$-alkenyl, $C_6$–$C_{20}$-aryl, $C_7$–$C_{20}$-alkylaryl or $C_7$–$C_{20}$-arylalkyl radicals, optionally containing Si or Ge atoms; and p is an integer ranging from 0 to 3, being equal to the oxidation state of the metal M minus two; the two double bonds in each of the cyclopentadienyl rings of said ligand being in any of the allowed positions.

5. A ligand of formula (III):

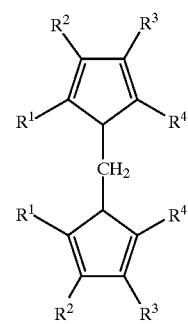

(II)

and its double bond isomers, wherein $R^1$, $R^2$, $R^3$ and $R^4$ have the meaning reported in claim 4.

6. A catalyst system for the polymerization of olefins comprising the product obtainable by contacting:

(A) one or more bridged metallocene compounds of formula (III) as described in claim 1; and (B) a suitable activating cocatalyst.

7. The catalyst system according to claim 6, wherein said activating cocatalyst is an alumoxane and/or a compound able to form an alkylmetallocene cation.

8. A process for the polymerization of olefins comprising the polymerization reaction of one or more olefin monomers in the presence of a catalyst system as described in claim 6.

9. The process according to claim 8, wherein said olefin monomer is propylene.

10. The process for the polymerization of olefins according to claim 9, wherein propylene is polymerized in the presence of a bridged metallocene as described in claim 1.

11. A process for the oligomerization of olefins comprising oligomerizing one or more olefin monomers in the presence of a bridged metallocene compounds as described in claim 1.

12. The process for the oligomerization of olefins according to claim 11, wherein said olefin is propylene.

13. The bridge metallocene compound according to claim 1, wherein M is Ti, Zr or Hf.

14. The bridge metallocene compound according to claim 1, wherein X is either chlorine or methyl.

* * * * *

UNITED STATES PATENT AND TRADEMARK OFFICE
CERTIFICATE OF CORRECTION

PATENT NO. : 6,268,518 B1
DATED : July 31, 2001
INVENTOR(S) : Luigi Resconi et al.

It is certified that error appears in the above-identified patent and that said Letters Patent is hereby corrected as shown below:

<u>Column 26,</u>
Line 2, please delete "of";
Line 58, please change "compounds" to -- compound --.

Signed and Sealed this

Sixteenth Day of April, 2002

Attest:

JAMES E. ROGAN
*Director of the United States Patent and Trademark Office*

*Attesting Officer*